US009108908B2

(12) United States Patent
Caillol et al.

(10) Patent No.: US 9,108,908 B2
(45) Date of Patent: Aug. 18, 2015

(54) METHOD FOR FUNCTIONALIZING NATURAL FATTY SUBSTANCES

(75) Inventors: Sylvain Caillol, Montpellier (FR); Bernard Boutevin, Montpellier (FR); Myriam Desroches, Montpellier (FR)

(73) Assignees: CENTRE NATIONAL DE LA RECHERCHE SCIENTIFIQUE (C.N.R.S.), Paris (FR); ECOLE NATIONALE SUPERIEURE DE CHIMIE DE MONTPELLIER, Montpellier Cedex (FR); UNIVERSITE MONTPELLIER 2, SCIENCES ET TECHNIQUES, Montpellier Cedex (FR)

( * ) Notice: Subject to any disclaimer, the term of this patent is extended or adjusted under 35 U.S.C. 154(b) by 109 days.

(21) Appl. No.: 13/807,146

(22) PCT Filed: Jun. 30, 2011

(86) PCT No.: PCT/FR2011/051532
§ 371 (c)(1),
(2), (4) Date: Jan. 29, 2013

(87) PCT Pub. No.: WO2012/001315
PCT Pub. Date: Jan. 5, 2012

(65) Prior Publication Data
US 2013/0123456 A1    May 16, 2013

(30) Foreign Application Priority Data
Jun. 30, 2010 (FR) ...................................... 10 02738

(51) Int. Cl.
C08G 65/14 (2006.01)
C07C 319/18 (2006.01)
C11C 3/00 (2006.01)

(52) U.S. Cl.
CPC .................. C07C 319/18 (2013.01); C11C 3/00 (2013.01)

(58) Field of Classification Search
CPC ................................. C11C 3/00; C07C 319/18
USPC .......................................................... 528/101
See application file for complete search history.

(56) References Cited
U.S. PATENT DOCUMENTS 4,566,878 A * 1/1986 Karol et al. ..................... 44/383
7,989,647 B2   8/2011 Geiger et al.

2006/0009365 A1   1/2006 Erhan et al.
2011/0313074 A1   12/2011 Geiger et al.
2012/0283467 A1   11/2012 Cramail et al.

FOREIGN PATENT DOCUMENTS

WO    WO 02/100991        12/2002
WO    WO 2011045536 A1 *   4/2011 ............ C07C 323/52

OTHER PUBLICATIONS

Guo et al, "Polyols and Polyurethanes from Hydroformylation of Soybean Oil", Apr. 2002, pp. 49-52, vol. 10, Nos. ½, Journal of Polymers and the Environment.
Sharma et al, Synthesis of Hydroxy Thio-ether Derivatives of Vegetable Oil, Dec. 5, 2006, pp. 9866-9872, vol. 54, No. 26, J. Agric. Food Chem.
International Search Report for PCT/FR2011/051532 dated Nov. 9, 2011.
Lluch Cristina et al: "Rapid Approach to Biobased Telechelics through Two One-Pot Thiol-Ene Click Reactions", Biomacromolecules, vol. 11, No. 6, (May 12, 2010), pp. 1646-1653.
Bantchev Grigor B et al: "Free Radical Addition of Butanethiol to Vegetable Oil Double Bonds", Journal of Agricultural and Food Chemistry, vol. 57, No. 4, (Feb. 2009), pp. 1282-1290.
Samuelsson J et al: "Thiol-ene coupling reaction of fatty acid monomers", Journal of Polymer Science, Part A: Polymer Chemistry 20041215 John Wiley and Sons Inc. US, vol. 42, No. 24, (Dec. 15, 2004), pp. 6346-6352.
Lowe, Andrew B.: "Thiol-ene "click" reactions and recent applications in polymer and materials synthesis", Polymer Chemistry, vol. 1, No. 1, (Nov. 25, 2009), pp. 17-36.

* cited by examiner

*Primary Examiner* — Michael L Leonard
(74) *Attorney, Agent, or Firm* — B. Aaron Schulman, Esq.; Stites & Harbison, PLLC.

(57) ABSTRACT

The invention relates to a method for functionalizing natural fatty substances: According to said method, plant oils including at least two unsaturations and the derivatives thereof, fatty acids including at least one unsaturated compound and the derivatives thereof, and mixtures of same, are reacted with a thiol derivative of formula (I), at a temperature of between 0° C. and the temperature of total degradation of the natural fatty substance and in the presence of a thermal initiator compound or a redox initiator, or by UV radiation, or by UV radiation and in the presence of a photoinitiator. The invention also relates to the resulting functionalized fatty substances and to the use thereof for the preparation of polymers. The invention further relates to a method for preparing polymers from at least one functionalized fatty substance obtained by said functionalization method.

23 Claims, No Drawings

METHOD FOR FUNCTIONALIZING NATURAL FATTY SUBSTANCES

The present invention concerns a method for functionalizing fatty substances of natural origin and the functionalized fatty substances thus obtained. The present invention also concerns the use of the functionalized fatty substances obtained for the preparation of polymers. Finally, the invention concerns a method for preparing polymers from at least one functionalized fatty substance obtained using the said functionalization method.

Vegetable oils and the derivatives thereof can be the subject of numerous chemical modifications involving their unsaturations. In particular, the adding of reactive functions allows the use of these modified oils as agriculturally-sourced compounds for polymer production, replacing non-natural compounds which may be toxic.

Different techniques have been described for adding reactive functions to fatty substances of natural origin.

Particular mention can be made of epoxidation reactions followed by hydrolysis allowing the preparation of functionalized fatty substances by secondary alcohols. This type of method has particularly been described in patent application WO-2006/094227. This method remains the most frequently used in industry for the functionalization of oils. However, secondary alcohols have limited reactivity compared with primary alcohols.

It is therefore of importance to provide a method for functionalizing natural fatty substances with the use in particular of primary alcohol functions.

The hydroformylation of oils described in particular by A. Guo et al. (Journal of Polymers and The Environment, 2002, 10 (1/2), 49-52) gives access to aldehyde functions which, after hydrogenation, provide access to primary alcohols.

Diels-Alder reactions have also been used to give access to functional derivatives.

Other authors, in particular Sharma et al (Journal of Agricultural and Food Chemistry, 2006, 54 (26), 9866-9872; and US-2006/0009365) have developed a method for producing functionalized fatty substances comprising an epoxidation step followed by an addition step of thiol, in particular butanethiol. The compounds obtained are described as lubricants especially in the automotive sector.

All these methods have the disadvantage of requiring several steps and at times costly reagents or catalysts which are often toxic.

Studies have been conducted on the modification of the double bonds of fatty substances by thiol-ene reaction. The publication by Samuelsson et al (Journal of Polymer Science, Part A: Polymer Chemistry, 2004, 42, 6346-6352) can be cited in particular which describes the reaction of thiol-ene coupling on fatty acid monomers. Bantchev et al (Journal of Agricultural and Food Chemistry, 2009, 57(4), 1282-1290) also disclose the thiol-ene reaction on vegetable oils and the use of the product obtained as lubricant.

However, these two methods do not use functionalized thiols and therefore do not allow the adding of reactive functions onto natural fatty substances. The fatty substances obtained with these methods cannot be used for the production of polymers, in particular by polycondensation.

There is a need for a method with which it is possible, in a single step, to add reactive functions onto natural fatty substances.

It is one of the objectives of the invention to provide a method that is simple and low-cost for functionalizing a natural fatty substance in a single step. The invention therefore allows the preparation of polyfunctional derivatives in a single step, avoiding the disadvantages of prior art methods.

Another objective of the invention is to produce products derived from agriculturally-sourced reagents that are carriers of reactive functions, in particular alcohol, acid functions, etc.

A further objective of the invention is to provide synthons of functionalized fatty substance type of natural origin for polymer synthesis.

A further objective of the invention is to provide a novel method for synthesizing polymers fully or partly derived from bio-sourced reagents.

The invention concerns a method for preparing, in a single step, a fatty substance functionalized by reactive functions. The method of the invention uses a reaction of thiol-ene type.

The invention concerns the application of the thiol-ene reaction to add reactive functions to fatty substances of natural origin.

The present invention concerns a method for preparing a functionalized fatty substance comprising the reaction of a natural fatty substance chosen from among:
vegetable oils comprising at least two unsaturations, and their derivatives;
fatty acids comprising at least one unsaturation and their derivatives;
the mixtures thereof with a thiol derivative of formula (I)

$$G_n\text{-}L^1\text{-}L^2\text{-SH} \qquad (I)$$

where:
G, the same or different, represents —OH; —NR$^1$H; —C(O)OH;

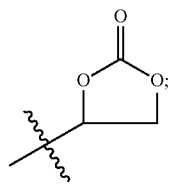 [SMILES: *C1COC(=O)O1]

—C(O)H;
n is 1 or 2;
R$^1$ is a hydrogen atom; a C$_1$-C$_{10}$ preferably C$_1$-C$_6$ alkyl radical, linear or branched, preferably methyl, ethyl, non-substituted or substituted by at least one group chosen from among —OH, —C(O)OH, —NH$_2$, —C(O)H,

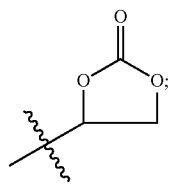 [SMILES: *C1COC(=O)O1]

L$^1$ is a —CH$_2$ group or a direct bond;
L$^2$ is:
a C$_1$-C$_{20}$ preferably C$_1$-C$_{20}$ alkyl, linear or branched, preferably methyl, ethyl, propyl, butyl, pentyl, hexyl, heptyl, octyl, nonyl, decyl, undecyl, dodecyl, optionally comprising one or more heteroatoms chosen from among an oxygen atom, a nitrogen atom, a sulfur atom, non-substituted or substituted by at least one group chosen from among —OH, —C(O)OH, —C(O)H,

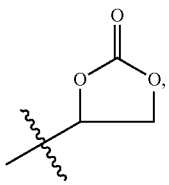 [SMILES: *C1COC(=O)O1]

—NHR² where R² is a hydrogen atom; a $C_1$-$C_{10}$ preferably $C_1$-$C_6$ alkyl radical, linear or branched, preferably methyl, ethyl, non-substituted or substituted by at least one group chosen from among —OH, —C(O)OH, —NH₂, —C(O)H,

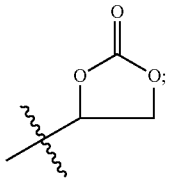 [SMILES: *C1COC(=O)O1]

a $C_3$ to $C_8$, carbo- or heterocycle, in particular a cycloaliphatic group, an aryl group preferably phenyl, a heteroaryl group preferably pyridine;

at a temperature of between 0° C. and the total degradation temperature of the natural fatty substance and in the presence of a thermal initiator or a redox initiator, or:

under the action of UV radiation, or under the action of UV radiation in the presence of a photoinitiator.

According to the invention, the vegetable oil and its derivatives comprise between 2 and 20 unsaturations.

The vegetable oil can be chosen from among crude or purified natural vegetable oils, and vegetable oils derived from genetically modified plants or cultures.

According to the invention, the vegetable oil is chosen from among canola oil, safflower oil, rapeseed oil, cottonseed oil, linseed oil, corn oil, hazelnut oil, coconut oil, olive oil, palm oil, grape-seed oil, castor oil, sesame oil, soybean oil, sunflower oil, alone or in a mixture.

The derivatives of vegetable oils can be chosen from among the fatty esters obtained by esterification or transesterification of vegetable oils, in particular the vegetable oils according to the invention; fatty amides obtained by amidification or transamidification of a vegetable oil, in particular a vegetable oil according to the invention, and partly epoxidized vegetable oils in particular those according to the invention.

By partly epoxidized vegetable oils is meant vegetable oils in which part of the unsaturations have been epoxidized and of which at least two unsaturations have not reacted, preferably between 20 and 80%, more preferably between 30 and 50% of the unsaturations are epoxidized.

In general, by (trans)esterification and (trans)amidification is meant reactions which take place on the terminal function of the constituent triglycerides of the vegetable oil, and by epoxidation is meant a reaction taking place on the unsaturations of the vegetable oil.

According to the invention, the fatty acids and their derivatives comprise between 1 and 6 unsaturations.

According to the invention, the fatty acids are chosen from among arachidonic acid, docosahexaenoic acid, eicosapentaenoic acid, erucic acid, linoleic acid, linolenic acid, nervonic acid, oleic acid, palmitoleic acid, ricinoleic acid, vernolic acid. The fatty acids may also be obtained from the vegetable oils according to the invention.

The derivatives of fatty acids are especially chosen from among the esters of fatty acids, for example methyl oleate, the fatty amides obtained by amidification of fatty acids, and the fatty thioesters derived from thioesterification of fatty acids, in particular the fatty acids according to the invention.

Preferably, the invention concerns a method in which G, the same or different, represents —NR¹H;

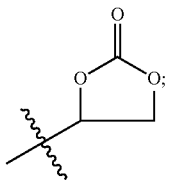 [SMILES: *C1COC(=O)O1]

—C(O)OH; —C(O)H, R¹ being such as defined above.

Also preferably, the invention concerns a method in which G the same or different represents —OH, —C(O)OH, —NH₂, —C(O)H,

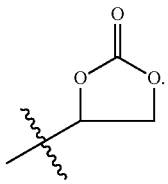 [SMILES: *C1COC(=O)O1]

Also preferably, the invention concerns a method in which G, the same or different, represents —C(O)OH, —NH₂, —C(O)H,

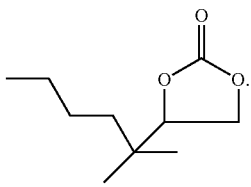

Preferably n is 1.

Preferably, the invention concerns a method in which L² represents a phenyl or a $C_1$-$C_{20}$ preferably $C_1$-$C_{12}$ alkyl chain, linear or branched, preferably methyl, ethyl, propyl, butyl, pentyl, hexyl, heptyl, octyl, nonyl, decyl, undecyl, dodecyl.

According to the invention, the invention concerns a method in which the thiol derivative of formula (I) is chosen from among cysteamine (2-aminoethanethiol), thioglycolic acid (mercaptoacetic acid), β-mercaptoethanol, mercaptosuccinic acid (thiomalic acid), 3-mercaptopropionic acid, 1-thiolglycerol (3-mercapto-1,2-propanediol), cysteine, 3-mercapto-1-propanol, 4-mercapto-1-butanol, 4-mercaptophenol, 4-aminothiophenol, 6-mercaptohexanoic acid, 3-mercaptobenzoic acid, thiosalicylic acid, 2-mercapto-benzyl alcohol, 4-mercaptophenylacetic acid, 8-mercaptooctanoic acid, 9-mercapto-1-nonanol, 12-mercaptododecanoic acid, 3-mercaptobutanal, 3-mercaptohexanal.

Preferably, the invention concerns a method in which the thiol derivative of formula (I) is chosen from among cysteamine (2-aminoethanethiol), thioglycolic acid (mercaptoacetic acid), mercaptosuccinic acid (thiomalic acid), 3-mercaptopropionic acid, 1-thiolglycerol (3-mercapto-1,2-propanediol), cysteine, 4-mercaptophenol, 4-aminothiophenol, 6-mercaptohexanoic acid, 3-mercaptobenzoic acid, thiosalicylic acid, 2-mercapto-benzyl alcohol, 4-mercaptophenylacetic acid, 8-mercaptooctanoic acid, 12-mercaptododecanoic acid, 3-mercaptobutanal, 3-mercaptohexanal.

Preferably, the invention concerns a method in which the thiol derivative of formula (I) is chosen from among cysteamine (2-aminoethanethiol), thioglycolic acid (mercaptoacetic acid), mercaptosuccinic acid (thiomalic acid), 3-mercaptopropionic acid, cysteine, 4-aminothiophenol, 6-mercaptohexanoic acid, 3-mercaptobenzoic acid, thiosalicylic acid, 2-mercapto-benzyl alcohol, 4-mercaptophenylacetic acid, 8-mercaptooctanoic acid, 12-mercaptododecanoic acid, 3-mercaptobutanal, 3-mercaptohexanal.

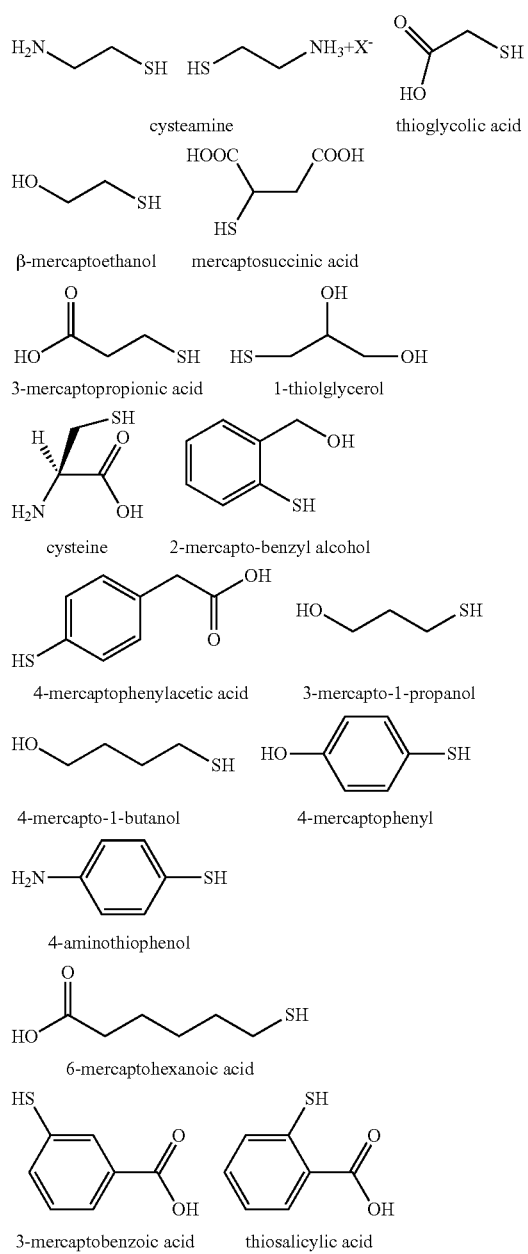

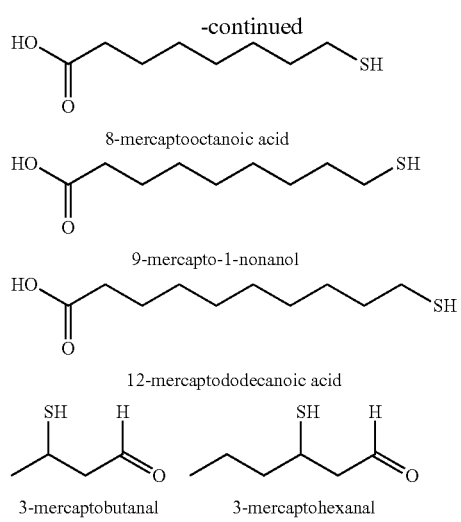

According to the invention, the method can be conducted at a temperature of between 0° C. and the total degradation temperature of the natural fatty substance, and in the presence of a thermal initiator compound or redox initiator.

By total degradation temperature of the natural fatty substance is meant the temperature on and after which all the unsaturations of the said fatty substance are hydrogenated. Said temperature depends on the fatty substance and is known or can be determined.

Preferably, the temperature is between ambient temperature and the total degradation temperature of the natural fatty substance, preferably it is between ambient temperature and 250° C., more preferably between 40° C. and 150° C.

By thermal initiator is meant any type of initiator generating radicals via thermal decomposition. The following can be cited in particular: azobisisobutyronitrile (AIBN), benzoyl peroxide, tert-amyl peroxypivalate, boranes, bis(4-tert-butylcyclohexyl)peroxydicarbonate.

By redox initiator is meant any type of initiator for which the production of radicals results from an oxidation-reduction reaction. Particular mention can be made of the tert-butylperbenzoate/erythorbic acid system, benzoyl peroxide/amine, $H_2O_2/Fe^{2+}$ (Femton reagent). The choice of initiator depends on the temperature at which the method is conducted and can be determined in accordance with the reaction conditions.

Particular mention can be made of the use of AIBN, but not limited thereto, at a temperature of 85° C., or the use of tert-amyl peroxypivalate at a temperature of 50° C.

According to the invention, the method can be conducted under UV radiation and optionally in the presence of a photochemical initiator (photoinitiator).

By photochemical initiator or photoinitiator is meant any type of initiator generating radical under the action of UV radiation. As an example, mention can be made of benzyl.

The choice of initiator depends on the wavelength of UV radiation used, and can be determined in accordance with the reaction conditions.

In general, the wavelength of the UV radiation is between 200 and 800 nm, preferably between 250 and 500 nm.

Preferably, the method of the invention is implemented under the action of UV radiation or under the action of UV radiation in the presence of a photoinitiator.

Advantageously, the method of the invention is implemented under the action of UV radiation.

The method of the invention can be implemented with or without a solvent. A solvent is used in systems which may give rise to solubility problems, in particular solubility of the initiator.

The method of the invention can be conducted in the presence of a solvent which, if the method is implemented under UV radiation, must be UV-transparent.

The solvents which can be used in the method at the temperature of and in the presence of a thermal initiator are notably chosen from among tetrahydrofuran, toluene, pentane, hexane, heptane, cyclohexane, methanol, ethanol, ethyl acetate, diethyl ether, dioxane, chloroform, acetonitrile, dichloromethane, dichloroethane, water, green solvents of succinate type, alone or in a mixture.

The solvents which can be used in the method under UV radiation are particularly chosen from among methanol, ethanol.

For the method of the invention, the following characteristics can be combined in full or in part:

G represents —OH; —NR$^1$H; —C(O)OH;

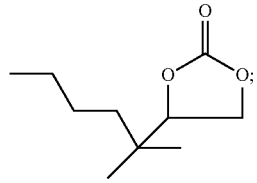

—C(O)H, preferably G is —NR$^1$H; —C(O)OH;

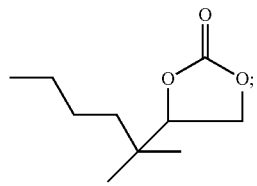

—C(O)H;

L$^1$ is a —CH$_2$ group; a direct bond;

L$^2$ is:

a $C_1$-$C_{20}$ preferably $C_1$-$C_{12}$ alkyl, linear or branched, preferably methyl, ethyl, propyl, butyl, pentyl, hexyl, heptyl, octyl, nonyl, decyl, undecyl, dodecyl, optionally comprising one or more heteroatoms chosen from among an oxygen atom, a nitrogen atom, a sulfur atom, non-substituted or substituted by at least one group chosen from among —OH, —C(O)OH, —C(O)H,

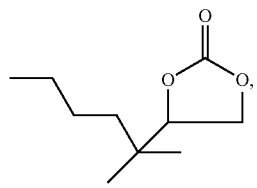

—NHR$^2$ where R$^2$ is a hydrogen atom; a $C_1$-$C_{10}$ preferably $C_1$-$C_6$ alkyl radical, linear or branched, preferably methyl, ethyl, non-substituted or substituted by at least one group chosen from among: —OH, —C(O)OH, —NH$_2$, —C(O)H,

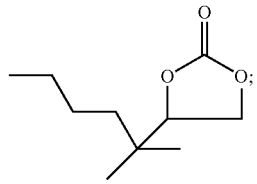

a $C_3$ to $C_8$, carbo- or heterocycle, in particular a cycloaliphatic group, an aryl group preferably phenyl, a heteroaryl group preferably pyridine;

temperature between 0° C. and the total degradation temperature of the natural fatty substance, preferably between ambient temperature the total degradation temperature of the natural fatty substance, more preferably between ambient temperature and 250° C., further preferably between 40° C. and 150° C. and a thermal or redox initiator;

use of UV radiation;

use of UV radiation and a photochemical initiator.

Advantageously, the invention concerns a method in which G is chosen from among —OH and NHR$^1$, where R$^1$ is according to the invention, preferably R$^1$ represents H, and the method is conducted under UV radiation.

Preferably, the invention concerns a method in which G represents NHR$^1$, where R$^1$ is according to the invention, preferably R$^1$ represents H, and the method is conducted under UV radiation.

Also advantageously, the invention concerns a method in which G is chosen from among —OH, —C(O)OH and the method is conducted at a temperature of between 0° C. and the total degradation temperature of the natural fatty substance, preferably between ambient temperature and the total degradation temperature of the natural fatty substance, more preferably between ambient temperature and 250° C., further preferably between 40° C. and 150° C.

Preferably, the invention concerns a method in which G represents —C(O)OH and the method is conducted at a temperature of between 0° C. and the total degradation temperature of the natural fatty substance, preferably between ambient temperature and the total degradation temperature of the natural fatty substance, more preferably between ambient temperature and 250° C., further preferably between 40° C. and 150° C.

The method of the invention has the advantage of not requiring any multiple, extended purification steps. For example, simple purification by liquid/liquid extraction or distillation under reduced pressure and at low temperature is sufficient to obtain the functionalized fatty substance with a high degree of purity.

The method of the present invention advantageously allows a high rate of conversion and functionalization of the natural fatty substances, in particular of between 25 and 100%), preferably between 50 and 100%).

Another advantage of the method according to the invention is that it provides control over the mean functionalization rate of the natural fatty substance, for example by acting on the nature of the oil, and hence on the unsaturation level, or on the quantity of functional thiol that is used. It is therefore possible to adapt the method of the invention to the use subsequently made of the products obtained. In particular, the diversity of the oils of vegetable origin allows the oil to be chosen in relation to the desired functionalization. For each type of oil, the mean number of unsaturations is known. Table 1 gives an example of oils which can be used in the method of the invention and the number of unsaturations thereof.

TABLE 1

| Vegetable oils | Fatty acid (%) | | | | | | | | | | |
|---|---|---|---|---|---|---|---|---|---|---|---|
| | 16:0 | 18:0 | 20:0 | 22:0 | 18:1 | 18:2 | 18:3 | 18:1 (12OH) | 22:1 | Saturated | Unsaturated |
| Corn | 12 | 2 | | | 25 | 53 | | | | 21 | 79 |
| Cottonseed | 28 | 1 | | | 15 | 56 | | | | 29 | 71 |
| Linseed | 5 | 2 | | | 20 | 17 | 56 | | | 7 | 93 |
| Linseed (mutagenesis) | 6 | 3 | | | 15 | 73 | 3 | | | 9 | 91 |
| Hazelnut | 12 | 2 | 1 | 2 | 49 | 33 | 1 | | | 17 | 83 |
| Rapeseed | 3 | 1 | | | 64 | 23 | 8 | | 1 | 4 | 96 |
| Canola | 4 | 2 | | | 66 | 19 | 9 | | | 6 | 94 |
| Safflower | 9 | 1 | | | 12 | 78 | | | | 10 | 90 |
| Sesame | 13 | 4 | | | 53 | 30 | | | | 17 | 83 |
| Soybean | 13 | 3 | | | 23 | 55 | 6 | | | 16 | 84 |
| Soybean (genetic) | 7 | 4 | | | 85 | 1 | 2 | | | 12 | 88 |
| Sunflower | 6 | 3 | | | 17 | 74 | | | | 9 | 91 |
| Sunflower(mutagenesis) | 3 | 2 | | | 92 | 2 | | | | 6 | 94 |
| Castor oil | | | | | 2 | 6 | 1 | 89 | | 2 | 98 |
| Palm oil | 40 | 5 | | | 46 | 9 | | | | 45 | 55 |
| Olive oil | 11 | 2 | | | 78 | 9 | | | | 13 | 87 |
| Grapeseed oil | 8 | 4 | | | 17 | 76 | | | | 12 | 88 |
| Coconut oil | 8 | 3 | | | 7 | 1 | | | | 92 | 8 |

Fatty acids are defined by two values, the first representing the total number of carbons forming the chain, the second being the number of double bonds present on this chain.

16:0=palmitic acid, 18:0=stearic acid, 20:0=arachidic acid, 22:0=behenic acid, 18:1=oleic acid, 18:2=linoleic acid, 18:3=linolenic acid, 18:1(12OH)=ricinoleic acid, 22:1=erucic acid.

The invention also concerns a functionalized fatty substance able to be obtained with the method of the invention.

The invention also concerns a functionalized fatty substance of formula (IIa), (IIb) or (IIc):

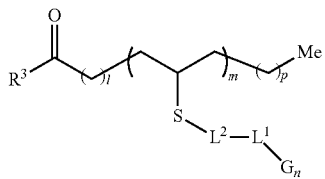
(IIa)

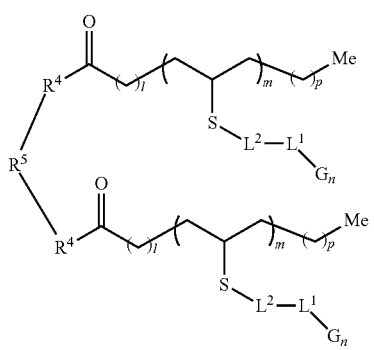
(IIb)

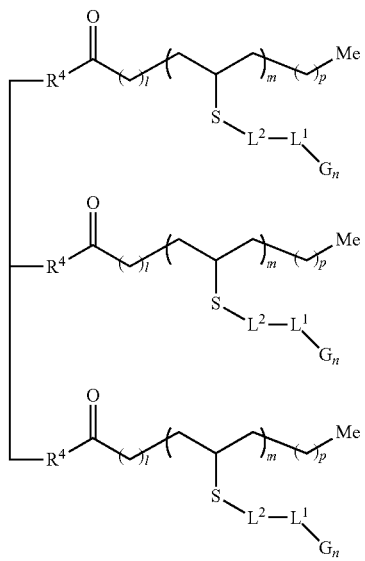
(IIc)

where:
G, the same or different, represents —OH; —NR$^1$H; —C(O)OH;

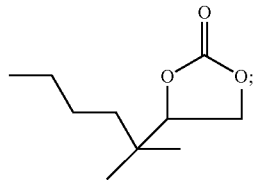

—C(O)H; n is 1 or 2;
R$^1$ is a hydrogen atom; a C$_1$-C$_{10}$ alkyl radical, linear or branched, non-substituted or substituted by at least one group chosen from among —OH, —C(O)OH, —NH$_2$, —C(O)H,

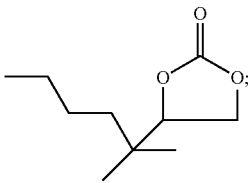

preferably $R^1$ is a hydrogen atom;
$L^1$ is a —$CH_2$ group; a direct bond;
$L^2$ is:
  a $C_1$-$C_{20}$ alkyl preferably $C_1$-$C_{12}$, linear or branched, preferably methyl, ethyl, propyl, butyl, pentyl, hexyl, heptyl, octyl, nonyl, decyl, undecyl, dodecyl, optionally comprising one or more heteroatoms chosen from an oxygen atom, a nitrogen atom, a sulfur atom, non-substituted or substituted by at least one group chosen among —OH, —C(O)OH, —C(O)H,

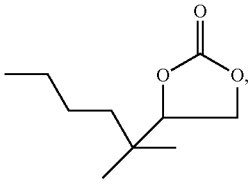

—$NHR^2$ where $R^2$ is a hydrogen atom; a $C_1$-$C_{10}$ preferably $C_1$-$C_5$, alkyl radical, linear or branched, preferably methyl, ethyl . . . , non-substituted or substituted by at least one group chosen from among —OH, —C(O)OH, —$NH_2$, —C(O)H,

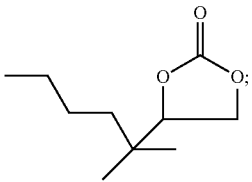

a $C_3$ to $C_8$, carbo- or heterocycle, in particular a cycloaliphatic group, an aryl group preferably phenyl, a heteroaryl group preferably pyridine;
$R^3$ is:
  a hydroxyl group (OH),
  an alkoxy group of type —OX, where X is chosen from among a $C_1$-$C_{20}$ preferably $C_1$-$C_{12}$ alkyl, linear or branched, optionally substituted by at least one group chosen from among —OH, —C(O)OH, —$NH_2$, —C(O)H,

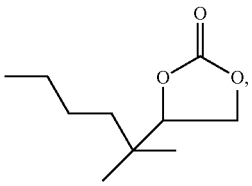

preferably methyl, ethyl, ethylene glycol, glycerol.
  an amine group -NY'Y", where Y' and Y", the same or different represent a hydrogen atom, a $C_1$-$C_{20}$ preferably $C_1$-$C_{12}$ alkyl, linear or branched, optionally substituted by at least one group chosen from among —OH, —C(O) OH, —$NH_2$, —C(O)H,

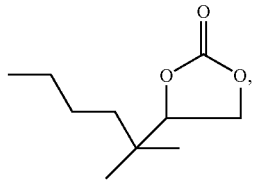

preferably methyl, ethyl, ethanolamine, diethanolamine; or ethylenediamine, 1,3-diaminopropane, hexamethylenediamine.
  a thio group of SZ type, with Z chosen among a $C_1$-$C_{20}$ preferably $C_1$-$C_{12}$ alkyl, linear or branched, optionally substituted by at least one group chosen from among —OH, —C(O)OH, —$NH_2$, —C(O)H,

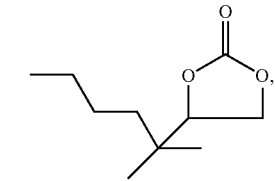

preferably cysteamine (2-aminoethanethiol), thioglycolic acid (mercaptoacetic acid), β-mercaptoethanol, mercaptosuccinic acid (thiomalic acid), 3-mercaptopropionic acid, 1-thiolglycerol (3-mercapto-1,2-propanediol), cysteine, 4-aminothiophenol, 6-mercaptohexanoic acid, 3-mercaptobenzoic acid, thiosalicylic acid, 4-mercaptophenylacetic acid, 8-mercaptooctanoic acid, 9-mercapto-1-nonanol, 12-mercaptododecanoic acid, 3-mercaptobutanal, 3-mercaptohexanal;
$R^4$ is:
  an oxygen atom;
  a nitrogen atom;
$R^5$ is:
  a $C_1$-$C_{20}$ preferably $C_1$-$C_{12}$ alkyl group, linear or branched, optionally substituted by at least one group chosen from among —OH, —C(O)OH, —$NH_2$, —C(O)H,

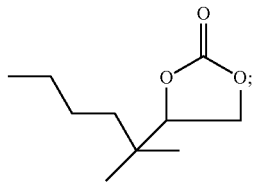

preferably methyl, ethyl, propyl, propanol;
l is an integer of between 1 and 10;
m is an integer of between 1 and 3;
p is an integer of between 0 and 10.

Preferably, the invention concerns a functionalized fatty substance of formula (IIa), (IIb) or (IIc), in which G, the same or different, represents —NR$^1$H; —C(O)OH;

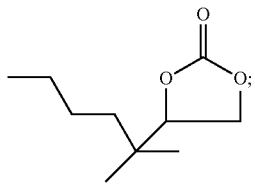

—C(O)H, R$^1$ being such as defined above.

Preferably, the invention concerns a functionalized fatty substance of formula (IIa), (IIb) or (IIc), in which G, the same or different, represents —OH, —C(O)OH, —NH$_2$, —C(O)H,

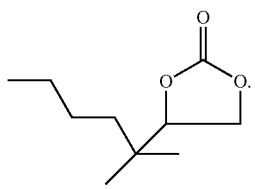

More preferably, the invention concerns a functionalized fatty substance of formula (IIa), (IIb) or (IIc), in which G, the same or different, represents —C(O)OH, —NH$_2$, —C(O)H,

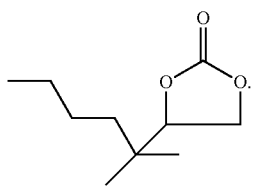

Preferably, the invention concerns a functionalized fatty substance of formula (IIa), (IIb) or (IIc), in which n is 1.

Preferably, the invention concerns a functionalized fatty substance of formula (IIa), (IIb) or (IIc), in which L$^2$ represents a phenyl or a C$_1$-C$_{20}$ preferably C$_1$-C$_{12}$ alkyl chain, linear or branched, preferably methyl, ethyl, propyl, butyl, pentyl, hexyl, heptyl, octyl, nonyl, decyl, undecyl, dodecyl.

Preferably, the invention concerns a compound of formula (IIa) according to the invention with the exception of the compounds of formulas (A) and/or (B)

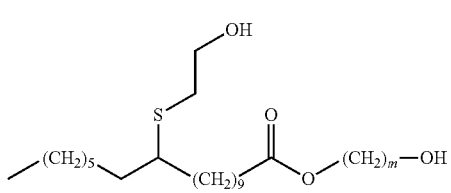

(A)

in which m is an integer ranging from 1 to 18, in particular from 1 to 12;

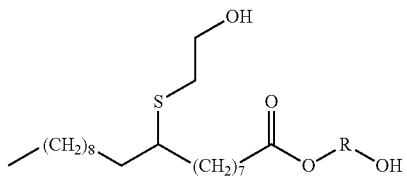

(B)

in which R represents C$_3$H$_6$, C$_4$H$_8$, C$_5$H$_{10}$ or C$_6$H$_{12}$.

Preferably, the invention concerns a compound of formula (IIa) according to the invention with the exception of the compound of formula (C):

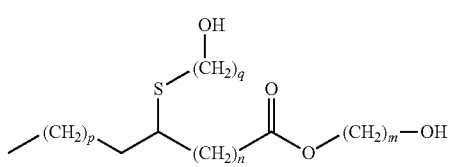

(C)

where:
m is an integer ranging from 1 to 18, in particular from 1 to 12;
n is an integer ranging from 2 to 11;
p is an integer ranging from 1 to 10; and
q is an integer ranging from 1 to 18, in particular from 1 to 13.

Preferably, the invention concerns a compound of formula (IIa) according to the invention with the exception of those in which n is 1, G represents —OH, L$^1$ represents a direct bond or a —CH$_2$— group, L$^2$ represents a C$_1$ to C$_{18}$, preferably C$_1$ to C$_{12}$, alkyl, R$^3$ represents an alkoxy group of formula —OX where X is a C$_1$ to C$_{18}$, preferably C$_1$ to C$_{12}$, alkyl radical substituted by an —OH group at terminal position, I is an integer ranging from 1 to 10; p is an integer ranging from 1 to 10; m is 1.

Preferably, the invention concerns a compound of formula (IIa) according to the invention with the exception of those in which R$^3$ represents an alkoxy group of formula —OX in which X represents a C$_1$ to C$_{18}$ in particular C$_1$ to C$_{12}$ alkyl radical, substituted by an —OH group at terminal position.

Preferably, the invention concerns a compound of formula (IIb) according to the invention with the exception of the compounds of formulas (D), (E), (F) and/or (G)

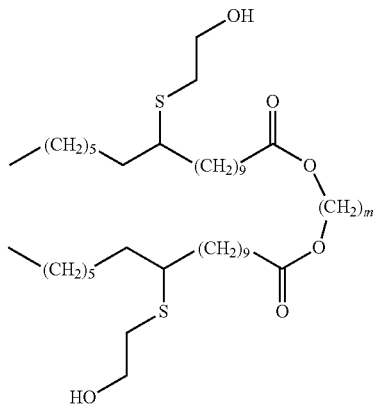

(D)

in which m is an integer ranging from 1 to 18, in particular from 1 to 12;

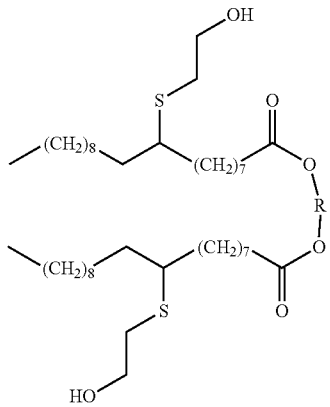
(E)

in which R represents $C_3H_6$, $C_4H_8$, $C_6H_{10}$, $C_6H_{12}$;

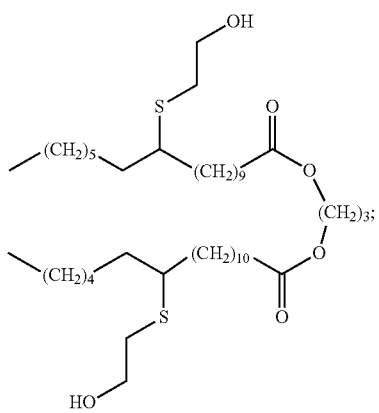
(F)

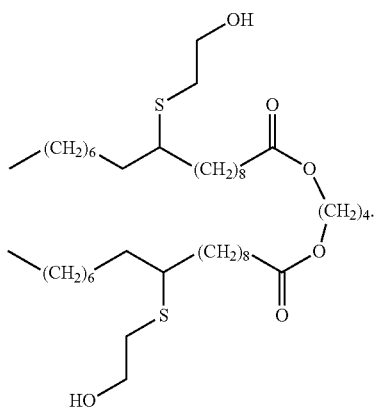
(G)

Preferably, the invention concerns a compound of formula (IIb) according to the invention with the exception of the compound of formula (H)

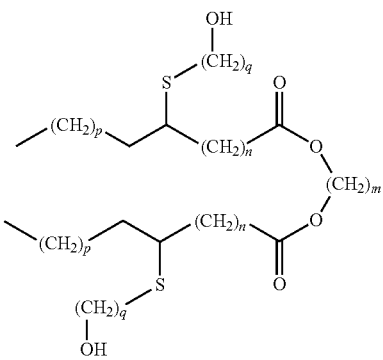
(H)

in which m is an integer ranging from 1 to 18, in particular from 1 to 12;
n is an integer ranging from 2 to 11;
p is an integer ranging from 1 to 10; and
q is an integer ranging from 1 to 18, in particular from 1 to 13.

Preferably, the invention concerns a compound of formula (IIb) according to the invention with the exception of those compounds in which n is 1, m is 1, G represents —OH, $L^1$ is a direct bond or a —CH$_2$— group, $L^2$ is a $C_1$ to $C_{18}$ in particular $C_1$ to $C_{12}$ alkyl, l is an integer ranging from 1 to 10, p is an integer ranging from 1 to 10, $R^5$ is an alkyl and $R^4$ an oxygen.

The functionalized fatty substance, either able to be obtained using the method of the invention or the functionalized fatty substance of the invention, comprises reactive G groups. It can therefore advantageously be used to prepare polymers via polycondensation.

A further subject of the invention concerns a method (a) for preparing a polymer which comprises:
(a1) preparing a functionalized fatty substance with the method of the invention,
(a2) polycondensation between the functionalized fatty substance obtained at step (a1) and at least one molecule at least bifunctional chosen from among isocyanates, alcohols, carboxylic acids, amines, carbamates, aldehydes, epoxy.

As examples, the following combinations can be cited:

| Functionalized fatty substance (a1) | Molecule, at least difunctional | Polymer obtained |
|---|---|---|
| G = OH | C(O)OH | polyester |
| G = NH$_2$ | C(O)OH | polyamide |
| G = NH$_2$ | ![cyclic carbonate] | polyurethane |
| G = NH$_2$ | ![epoxide] | epoxy resin |
| G = OH | NC(O) | polyurethane |

A further subject of the invention concerns a method (b) for preparing a polymer, comprising:
(b1) preparing a functionalized fatty substance using the method of the invention,
(b2) preparing a second functionalized fatty substance with the method of the invention, that is different and in which the G function is different from that of the fatty substance prepared at step (b1), then
(b3) polycondensation between the two functionalized fatty substances.

As examples the following combinations can be cited:

| Functlzd. fatty substances (b1) | Functlzd. fatty substances (b2) | Polymer obtained |
|---|---|---|
| G = OH | G = C(O)OH | polyester |
| G = NH$_2$ | G = C(O)OH | polyamide |
| G = NH$_2$ | 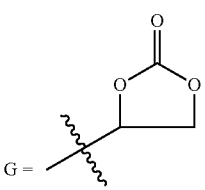 | polyurethane |

The invention also concerns the use either of a functionalized fatty substance able to be obtained using the method of the invention or a functionalized fatty substance of the invention for the preparation of a polymer.

According to the invention, it is possible to prepare a polymer chosen from among polyesters; polyamides; polycarbamates or polyisocyanates, in particular polyurethanes; epoxy resins; polycarbonates.

Advantageously, the use either of functionalized fatty substances able to be obtained according to the invention, or of functionalized fatty substances of the invention allows flexibility to be imparted to the polymer obtained by polycondensation.

Advantageously, the use either of functionalized fatty substances able to be obtained according to the method of the invention, or of functionalized fatty substances of the invention allows a reduction in and even the full removal of VOCs (Volatile Organic Compounds) during the preparation of a polymer compared with the compounds usually used for producing such polymers.

A TGA curve (5° C./min, 10° C./min and 20° C./min) of a commercial polyol (Desmophen® 1150) has been realized.

A TGA curve (5° C./min, 10° C./min and 20° C./min) of a polyol obtained with the method of the invention has been realized.

The invention will now be described with the help of non-limiting examples.

Example 1

Synthesis of a Functionalized Fatty Substance of Polyol Type Via Photochemical Route from Rapeseed Oil To a 10 mL quartz tube are added rapeseed oil (2 g, 2.3·10$^{-3}$ mol, i.e. about 8.6·10$^{-3}$ mol unsaturations) and β-mercaptoethanol (2.2 g, 2.8·10$^{-2}$ mol). The reaction medium is placed under UV irradiation from a mercury lamp equipped with a 250-450 nm filter and delivering an intensity of 15000 mW/cm$^2$. Strong agitation is continued throughout the entire duration of the reaction. After an exposure time of 5 hours, the reaction medium is diluted in ethyl acetate and the excess β-mercaptoethanol is washed three times with an aqueous sodium chloride solution. The organic phase is then dried with a desiccating agent of magnesium sulfate type and concentrated in a rotary evaporator in vacuo at 40° C. The polyol obtained is in the form of a viscous orangish liquid.

The absence of any signal at 5.40 ppm (C$\underline{H}$=C$\underline{H}$) and at 2.00 ppm (C$\underline{H}_2$—CH=) on the $^1$H NMR spectrum of the polyol indicates that the double bonds of the rapeseed oil have reacted. These disappearances are accompanied by the onset of signals characteristic of the adding of mercaptoethanol, in particular with the onset of the multiplet at 2.5 ppm characteristic of the proton belonging to the asymmetric alpha carbon of sulfur (C$\underline{H}$—S) of a multiplet at 1.53 ppm (C$\underline{H}_2$—CH—S) and at 1.40 ppm (C$\underline{H}_2$—CH$_2$—CH—S). Signals at 5.25 ppm (C$\underline{H}$—OCO), 4.26 and 4.16 ppm (C$\underline{H}_2$—OCO), 2.29 ppm (C$\underline{H}_2$—CO), 1.60 ppm (C$\underline{H}_2$—CH$_2$—CO), 1.26 ppm (CH$_2$—C$\underline{H}_2$—CH$_2$), 0.87 ppm (C$\underline{H}_3$—CH$_2$) are displayed, characteristic of the structure of the triglycerides.

The FTIR spectrum (Fourier Transform Infrared Spectrum) of the polyol provides confirmation of the disappearance of the double bonds of the rapeseed oil. The disappearance of the absorption band at 3008 cm$^{-1}$ (elongation CH sp2), and the decrease of the band at 721 cm$^{-1}$ (cis CC deformation) confirm the consumption of the double bonds of the rapeseed oil. The latter band does not disappear completely on account of the presence of the rocking CH$_2$ absorption band centred on the same wavelength number value. The appearance followed by the disappearance of a band at 964 cm$^{-1}$ is also noted (trans CC deformation). The onset of the broad band at 3400 cm$^{-1}$ confirms the set-up of OH functions. The formation of the CS bonds and the disappearance of the SH bonds are not visible using the FT-IR technique, since the intensity of the absorption bands expected at 600-700 cm$^{-1}$ and at 2500-2600 cm$^{-1}$ is too low.

Alcohol assay allows determination of the hydroxyl index when a fatty substance is functionalized by a thiol carrying an alcohol group. The method used provides access to the number of acid functions per unit weight of polyol (expressed in mg KOH/g of sample). About 0.5 g of sample are exactly weighed and mixed with 10 mL of an acetylated solution containing a pyridine/acetic anhydride mixture (88:12 by volume), in a 50 mL flask fitted with a coolant. After a reaction time of two hours at 100° C., the reaction medium is cooled down to ambient temperature then hydrolyzed with 100 mL of iced water. Under vigorous agitation, 20 mL of toluene are added and the solution is titrated with an aqueous KOH solution (0.5 mol/L), phenolphthalein acting as stained indicator. Three blanks are run and the hydroxyl number is given by the following formula:

$$I_{OH} = \frac{(V_{blanke} - V_{samplet}) \times 56.1 \times 0.5}{m_{sample}} + I_a$$

The assay of the carboxylic acid functions is performed for the purpose of calculating the exact values of the hydroxyl number. The hydroxyl number is based on acid-base assay and the presence of acid functions implies under-estimation of this number. This assay is performed using an ethanol potash solution, itself calibrated with a hydrochloric acid solution.

$I_a$=2.5 mg KOH/g
$I_{CH}$=187 mg KOH/g

The conversion of the double bonds reaches 98.5% and functionality is about f=3.94

The method of the invention conducted under UV radiation allows a functionalized fatty substance to be obtained with a high functionalization rate, and a high conversion rate of the double bonds of the vegetable oil.

Example 2

Synthesis of Polyurethane from the Polyol Obtained in Example 1

The polyol synthesized in Example 1 is mixed with methylene diphenyl 4,4'-diisocyanate (MDI) in the presence of dibutyltin dilaurate (DBTDL). The added quantities are given in Table 2 below. The mixture is brought to 120° C. for 2 hours.

TABLE 2

|  | Modified oil | MDI | DBTDL |
|---|---|---|---|
| Functionality | 3.94 | 2 | — |
| Weight (g) | 2 | 0.83 | 0.02 |
| Molar percentage (%) | 33.46 | 65.91 | 0.63 |

The reaction is quantitative, the yield is 100%.

The functionalized fatty substances of the invention or the fatty substances able to be obtained with the method of the invention allow the synthesis of polymers, in particular of polyurethane.

Example 3

Synthesis of a Functionalized Fatty Substance of Polyol Type Via Thermal Route from Rapeseed Oil To a two-necked 50 mL flask surmounted by a water coolant are added rapeseed oil (2 g, 2.3·10$^{-3}$ mol), mercaptoethanol (3.6 g, 4.6·10$^{-2}$ mol), dioxane (0.7 g, 7.5·10$^{-3}$ mol) and tert-amyl peroxypivalate (0.25 g, 1·10$^{-3}$ mol). The reaction medium is brought to 50° C. and held at this temperature for 24 hours. After synthesis, the product is purified by distillation under reduced pressure (10$^{-2}$ bars) and at low temperature (50° C.). The polyol obtained is a viscous orangish liquid.

The absence of any signal at 5.40 ppm (C$\underline{H}$=CH) and at 2.00 ppm (C$\underline{H}_2$—CH=) on the $^1$H NMR spectrum of the polyol indicates that the double bonds of the oleic acid have reacted. These disappearances are accompanied by the onset of signals characteristic of the addition of mercaptoethanol, in particular with the onset of the multiplet at 2.5 ppm characteristic of the proton belonging to the asymmetric alpha carbon of sulfur (C$\underline{H}$—S), of a multiplet at 1.53 ppm (C$\underline{H}_2$—CH—S) and at 1.40 ppm (C$\underline{H}_2$—CH$_2$—CH—S). Signals are noted at 5.25 ppm (C$\underline{H}$—OCO), 4.26 and 4.16 ppm (C$\underline{H}_2$—OCO), 2.29 ppm (C$\underline{H}_2$—CO), 1.60 ppm (C$\underline{H}_2$—CH$_2$—CO), 1.26 ppm (CH$_2$—C$\underline{H}_2$—CH$_2$), 0.87 ppm (C$\underline{H}_3$—CH$_2$) characteristic of the structure of the triglycerides.

The disappearance of the absorption band at 3008 cm$^{-1}$ (elongation CH sp2), and the decrease of the band at 721 cm$^{-1}$ (cis CC deformation) confirm the consumption of the double bonds. The onset of the broad band at 3400 cm$^{-1}$ confirms the setting-up of OH functions.

$I_a$=2.5 mg KOH/g $I_{OH}$=182 mg KOH/g

The conversion of the double bonds reaches 96% and functionality is about f=3.84.

With the method of the invention, performed at 50° C., it is possible to obtain functionalized fatty substances with a high functionalization rate and a high conversion rate of the double bonds of the starting vegetable oil.

Example 4

Synthesis of a Functionalized Fatty Substance of Fatty Diol Type Via Photochemical Route from Oleic Acid The esterification reaction is conducted in a 100 mL two-necked flask surmounted by apparatus of Dean Stark type. Once the ethylene glycol (4.4 g, 0.071 mol), oleic acid (4 g, 0.014 mol), acetone (8 g) and methanesulfonic acid (0.16 g, 1.6·10$^{-3}$ mol) have been added, the reaction medium is brought to 85° C. for 6 hours, solvent being regularly added. After synthesis, the solvent is removed by distillation then the product is purified by liquid-liquid extraction with an ethyl acetate/saturated aqueous sodium chloride system. The organic phase is dried with a desiccating agent of magnesium sulfate type and then concentrated in a rotary evaporator in vacuo at 40° C. The product is obtained in the form of a viscous brown liquid.

To a 10 mL quartz tube are added the previously synthesized oleic ester (2.5 g, 7.6·10$^{-3}$ mol) and β-mercaptoethanol (1.8 g, 2.3·10$^{-2}$ mol). The reaction medium is placed under UV radiation from a mercury lamp equipped with a 250-450 nm filter and delivering an intensity of 15000 mW/cm$^2$. Vigorous agitation is maintained throughout the reaction. After an exposure time of 2 hours, the reaction medium is diluted in ethyl acetate and the excess β-mercaptoethanol is washed three times with an aqueous sodium chloride solution. The organic phase is then dried with a desiccating agent of magnesium sulfate type, and concentrated in a rotary evaporator in vacuo at 40° C. The diol is obtained in the form of a viscous brown liquid.

The analyses performed are the same as for the synthesis of a polyol.

The $^1$H NMR spectrum of the diol exhibits signals at 4.20 ppm (C$\underline{H}_2$—OCO), 3.84 ppm (C$\underline{H}_2$—OH) indicating that esterification has indeed taken place. The absence of any signal at 5.40 ppm (C$\underline{H}$=C$\underline{H}$) and at 2.00 ppm (C$\underline{H}_2$—CH=) indicates that the double bonds of the oleic acid have reacted. These disappearances are accompanied by the onset of signals characteristic of the addition of mercaptoethanol, in particular with the onset of the multiplet at 2.5 ppm characteristic of the proton belonging to the asymmetric alpha carbon of sulfur (C$\underline{H}$—S) of a multiplet at 1.51 ppm (C$\underline{H}_2$—CH—S) and at 1.38 ppm (C$\underline{H}_2$—CH$_2$—CH—S). Signals are noted at 2.29 ppm (C$\underline{H}_2$—CO), 1.60 ppm (C$\underline{H}_2$—CH$_2$—CO), 1.26 ppm (CH$_2$—C$\underline{H}_2$—CH$_2$), 0.87 ppm (C$\underline{H}_3$—CH$_2$) characteristic of the structure of the fatty acids.

$I_a$=29 mg KOH/g $I_{OH}$=259 mg KOH/g

The conversion of the acid functions to ester reaches 85%), the conversion of the double bonds reaches 99% and functionality is about f=1.85.

The method of the invention implemented under UV radiation allows functionalized fatty substances to be obtained having a high functionalization rate and a high conversion rate of the double bonds of the starting fatty acid.

Example 5

Synthesis of a Functionalized Fatty Substance of Diol Type Via Photochemical Route from Rapeseed Oil To a 50 mL two-necked flask surmounted by Dean Stark apparatus are added the methyl esters of rapeseed oil (1.5 g, $5.0 \cdot 10^{-3}$ mol) and ethanolamine (0.4 g, $6.3 \cdot 10^{-3}$ mol). The reaction medium is brought to 100° C. and held under agitation for 15 hours. The reaction medium is cooled then solubilized in ethyl acetate, washed three times with an aqueous sodium chloride solution. The organic phase is then dried with a desiccating agent of magnesium sulfate type and concentrated in a rotary evaporator in vacuo at 40° C. The product is obtained in the form of an orangish solid.

To a 10 mL quartz tube are added the previously synthesized fatty amide (1 g, $3.1 \cdot 10^{-3}$ mol) and mercaptoethanol (2.6 g, $3.4 \cdot 10^{-2}$ mol), the mixture is homogenized by slight heating. The reaction medium is placed under UV radiation from a mercury lamp equipped with a 250-450 nm filter and delivering an intensity of 15000 mW/cm². Vigorous agitation is maintained throughout the entire duration of the reaction. After an exposure time of 5 hours, the reaction medium is diluted in ethyl acetate and the excess mercaptoethanol is washed three times in an aqueous sodium hydroxide solution. The organic phase is then dried with a desiccating agent of magnesium sulfate type, concentrated in a rotary evaporator in vacuo at 40° C. The fatty diol is obtained in the form of an orangish solid.

The signal at 3.43 ppm, characteristic of the alpha protons of the amide ($CH_2$—NHCO) indicates that amidification has indeed taken place. The absence of any signal at 5.40 ppm (C$H$=CH) and at 2.00 ppm ($CH_2$—CH=) on the $^1$H NMR spectrum of the end product indicates that the double bonds have reacted. These disappearances are accompanied by the onset of signals characteristic of the adding of mercaptoethanol, in particular with the onset of the multiplet at 2.58 ppm characteristic of the proton belonging to the asymmetric alpha carbon of sulfur (C$H$—S), and the onset of a multiplet at 1.52 ppm ($CH_2$—CH—S) and at 1.40 ppm (C$H_2$—$CH_2$—CH—S). Signals are noted at 2.21 ppm (C$H_2$—CO), 1.63 ppm ($CH_2$—$CH_2$—CO), 1.26 ppm ($CH_2$—C$H_2$—$CH_2$), 0.88 ppm ($CH_3$—$CH_2$) characteristic of the structure of the formed fatty amide.

$I_{OH}$=268 mgKOH/g

The conversion of the ester functions to amide reaches 100%, the conversion of the double bonds reaches 95% and functionality is about f=1.95.

The method of the invention implemented under UV radiation allows functionalized fatty substances to be obtained having a high functionalization rate and a high conversion rate of the double bonds of the starting vegetable oil or fatty acid.

Example 6

Synthesis of a Functionalized Fatty Substance of Fatty Diamine Type Via Photochemical Route from Methyl Oleate Amidification is carried out in 100 mL two-necked flask surmounted by Dean Stark apparatus. The methyl oleate (1.0 g, $3.4 \cdot 10^{-3}$ mol), 1,3-diaminopropane (0.6 g, $8.1 \cdot 10^{-3}$ mol) are held at 100° C. under agitation for 48 hours. The reaction medium is cooled then solubilized in ethyl acetate, washed three times in an aqueous sodium chloride solution. The organic phase is then dried with a desiccating agent of magnesium sulfate type and concentrated in rotary evaporator in vacuo at 40° C. The product is obtained in the form of a slightly yellow solid.

To a 10 mL quartz tube are added the previously synthesized fatty amide (1 g, $3.1 \cdot 10^{-3}$ mol), ethanol (3.7 g) and cysteamine (1.2 g, $1.1 \cdot 10^{-2}$ mol). The reaction medium is placed under UV radiation from a mercury lamp equipped with a 250-450 nm filter and delivering an intensity of 15000 mW/cm². Strong agitation is maintained throughout the entire duration of the reaction. After an exposure time of 5 hours, the reaction medium is diluted in ethyl acetate and the excess cysteamine is washed three times in an aqueous sodium hydroxide solution. The organic phase is dried with a desiccating agent of magnesium sulfate type then concentrated in a rotary evaporator in vacuo at 40° C. The fatty diamine is obtained in the form of an orangish solid.

In addition to the $^1$H NMR and FTIR analyses previously described, the amine assay allows verification of the functionalization of the fatty substances by a thiol carrying an amine group.

The presence on the $^1$H NMR diamine spectrum of the signals at 3.30 ppm ($CH_2$13 NHCO), 2.85 ppm ($CH_2$—$NH_2$) and the disappearance of the signal at 3.66 ppm characteristic of the starting methyl ester ($CH_3$—OCO) indicate that amidification has indeed occurred. The absence of any signal at 5.40 ppm (C$H$=C$H$) and at 2.00 ppm ($CH_2$—CH=) indicates that the double bonds of the starting methyl ester have reacted. These disappearances are accompanied by the onset of signals characteristic of the adding of cysteamine, in particular with the onset of the multiplet at 2.57 ppm characteristic of the proton belonging to the asymmetric alpha carbon of sulfur (C$H$—S), of a multiplet at 1.53 ppm ($CH_2$—CH—S) and at 1.39 ppm ($CH_2$—$CH_2$—CH—S). Signals at 2.20 ppm ($CH_2$—CONH), 1.60 ppm ($CH_2$—$CH_2$—CO), 1.26 ppm ($CH_2$—$CH_2$—$CH_2$), 0.87 ppm ($CH_3$—$CH_2$) are displayed, characteristic of the structure of the fatty acids.

Assay of the amine functions is based on acid-base assay. The sample is solubilized in distilled water acidified with HCl. The pH of the solution is lowered by adding hydrochloric acid (1 mol/L) down to a value of 1. The solution is then assayed with a sodium hydroxide solution (0.5 mol/L). Assay is followed by pHmetry, two equivalent volumes are detected. The amine number is then given by the following formula:

$$I_{NH2} = \frac{\Delta V_{eq} \times 0.5}{m_{ech}}$$

$I_{NH2}$=4.2·10⁻³ mol/g

The conversion of the ester functions to amide reaches 95%, the conversion of the double bonds reaches 80% and functionality is about f=1.8.

The method of the invention implemented under UV radiation allows functionalized fatty substances to be obtained with a high functionalization rate and a high conversion rate of the double bonds of the starting fatty acid.

Example 7

Synthesis of Functionalized Fatty Substances of Polyacid Type Via Thermal Route from Rapeseed Oil To a 100 mL two-necked flask surmounted by a coolant are added the rapeseed oil (2 g, $2.3 \cdot 10^{-3}$ mol, i.e. about $9.3 \cdot 10^{-3}$ mol unsaturations), thioglycolic acid (1.1 g, $1.1 \cdot 10^{-2}$ mol), and AIBN (0.2 g, $1.3 \cdot 10^{-3}$ mol) solubilized in ethyl acetate (1.4 g, $1.6 \cdot 10^{-2}$ mol). The reaction medium is brought to 40° C. and held under vigorous agitation for 48 hours. The reaction medium is diluted in ethyl acetate and the excess acid is washed three times in an aqueous sodium chloride solution to neutral pH of the washing waters. The organic phase is then dried with a desiccating agent of magnesium sulfate type and concentrated in a rotary evaporator in vacuo at 40° C. The polyacid is obtained in the form of a viscous orangish liquid. The absence of any signal at 5.40 ppm ($C\underline{H}=C\underline{H}$) and at 2.00 ppm ($C\underline{H}_2$—CH=) on the $^1$H NMR spectrum of the end product indicates that the double bonds of the rapeseed oil have reacted. These disappearances are accompanied by the onset of signals characteristic of the adding of thioglycolic acid, in particular with the onset of the multiplet at 2.76 ppm characteristic of the proton belonging to the asymmetric alpha carbon of sulfur (CH—S), and the onset of the singlet at 3.22 ppm ($C\underline{H}_2$—S), of a multiplet at 1.53 ppm ($C\underline{H}_2$—CH—S) and at 1.39 ppm ($C\underline{H}_2$—CH$_2$—CH—S). Signals at 5.27 ppm ($C\underline{H}$—OCO), 4.25 and 4.16 ppm ($C\underline{H}_2$—OCO), 2.31 ppm ($C\underline{H}_2$—CO), 1.59 ppm ($C\underline{H}_2$—CH$_2$—CO), 1.26 ppm (CH$_2$—$C\underline{H}_2$—CH$_2$), 0.87 ppm ($C\underline{H}_3$—CH$_2$) are displayed, characteristic of the structure of the triglycerides.

$I_a$=145 mg KOH/g

The conversion of the double bonds reaches 80% and functionality is about f=3.2.

The method of the invention, implemented at 40° C., allows functionalized fatty substances to be obtained having a high functionalization rate with a high conversion rate of the double bonds of the starting vegetable oil.

Example 8

Synthesis of a Functionalized Fatty Substance of <<Diacid>> Type Via Thermal Route from Rapeseed Oil To a 100 mL two-necked flask surmounted by a coolant are added the saponification product of rapeseed oil (1 g, $3.5 \cdot 10^{-3}$ mol, i.e. about $4.6 \cdot 10^{-3}$ mol unsaturations), thioglycolic acid (1.0 g, $1.1 \cdot 10^{-2}$ mol) and AIBN (0.1 g, $0.7 \cdot 10^{-3}$ mol) solubilized in ethyl acetate (0.7 g, $7.9 \cdot 10^{-3}$ mol). The reaction medium is brought to 40° C. and held under strong agitation for 48 hours. The reaction medium is diluted in ethyl acetate and the excess acid is washed three times in an aqueous sodium chloride solution until neutral pH of the washing waters. The organic phase is then dried with a desiccating agent of magnesium sulfate type and concentrated in a rotary evaporator in vacuo at 40° C. The diacid is obtained in the form of a viscous orangish liquid.

The absence of any signal at 5.40 ppm ($C\underline{H}=C\underline{H}$) and at 2.00 ppm ($C\underline{H}_2$—CH=) on the $^1$H NMR spectrum of the end product indicates that the double bonds of the rapeseed oil have reacted. These disappearances are accompanied by the onset of signals characteristic of the adding of thioglycolic acid, in particular with the onset of the multiplet at 2.76 ppm characteristic of the proton belonging to the asymmetric alpha carbon of sulfur (CH—S), and the onset of the singlet at 3.22 ppm ($C\underline{H}_2$—S), of a multiplet at 1.53 ppm ($C\underline{H}_2$—CH—S) and at 1.39 ppm ($C\underline{H}_2$—CH$_2$—CH—S). Signals are displayed at 2.31 ppm ($C\underline{H}_2$—CO), 1.59 ppm ($C\underline{H}_2$—CH$_2$—CO), 1.26 ppm (CH$_2$—$C\underline{H}_2$—CH$_2$), 0.87 ppm ($C\underline{H}_3$—CH$_2$), characteristic of the structure of the fatty acids.

$I_a$=192 mg KOH/g

The conversion of the double bonds reaches 86% and functionality is about f=2.14.

The method of the invention, implemented at 40° C., allows functionalized fatty substances to be obtained having a high functionalization rate with a high conversion rate of the double bonds of the starting vegetable oil.

Example 9

Synthesis of Epoxy Resin from the Polyacids Obtained According to Examples 7 and 8

The functionalized fatty acid and the rapeseed oil functionalized in Examples 7 and 8 are mixed with Bisphenol A diglycidyl ether (BADGE) in the presence of imidazole. The amounts added are given in Table 3. The mixture is brought to 105° C. for 24 hours. The material obtained is flexible and of shiny appearance.

TABLE 3

|  | Modified fatty oil | Modified fatty acid | BADGE | Imidazole |
|---|---|---|---|---|
| Acid number (mg KOH/g) | 144.9 | 192.3 | — | — |
| Weight (g) | 1.1 | 1.92 | 2.24 | 0.0262 |
| Mole percentage (%) | 9.25 | 39.25 | 48.5 | 3 |

The reaction is quantitative, the yield is 100%.

The functionalized fatty substances of the invention or the fatty substances able to be obtained with the method of the invention allow the synthesis of epoxy resin.

Example 10

TGA Curves (5° C./min, 10° C./min and 20° C./min) of a Commercial Polyol and a Polyol Obtained by Functionalizing a Vegetable Oil The thermal resistance of the polyols synthesized using the method of the invention and of commercial polyols was analyzed by TGA (Thermal Gravimetric Analysis) using TGA-Q50 apparatus, TA Instruments, equipped with a platinum pan, aluminium cups, under a constant stream of nitrogen and a temperature ramp of between 20° C. and 500° C. Each polyol was tested for three heating rates: 5° C./min, 10° C./min, 20° C./min.

A TGA curve (5° C./min, 10° C./min and 20° C./min) of a commercial polyol (Desmophen® 1150) has been realized.

A TGA curve (5° C./min, 10° C./min and 20° C./min) of a polyol obtained with the method of the invention has been realized.

The results obtained show that the fatty substances functionalized according to the invention have a degradation temperature higher than that of commercial polyols. Therefore, when the polyols of the invention are used in the synthesis of other polymers they allow the amount of released VOCs to be limited.

The invention claimed is:
1. A functionalized fatty substance selected from the group consisting of the compounds of formulas (IIa), (IIb) and (IIc):

(IIa)
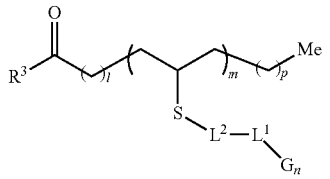

(IIb)
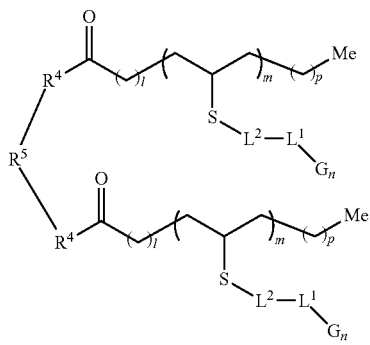

(IIc)
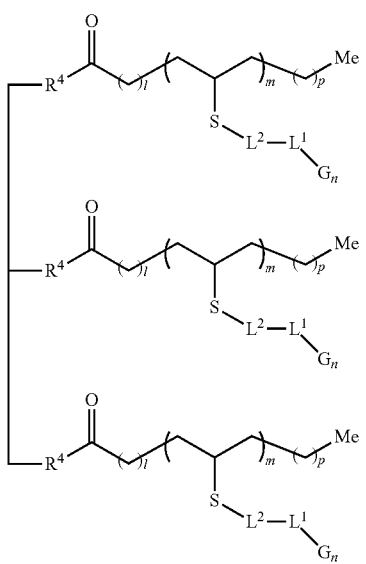

in which:
G, the same or different, represents $NR^1H$; —C(O)OH;

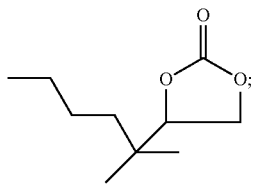

or —C(O)H;
n is 1 or 2;
$R^1$ is a hydrogen atom; a $C_1$-$C_{10}$ radical alkyl, linear or branched, non-substituted or substituted by at least one group selected from the group consisting of —OH, —C(O)OH, —NH$_2$, —C(O)H, and

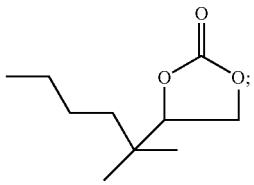

$L^1$ is a —CH$_2$ group; a direct bond;
$L^2$ is:
 a $C_1$-$C_{20}$ alkyl, linear or branched, optionally comprising one or more heteroatoms chosen from among an oxygen atom, nitrogen atom, sulfur atom, non-substituted or substituted by at least one group chosen among —OH, —C(O)OH, —C(O)H,

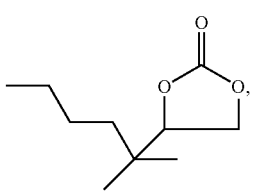

—NHR$^2$ where R$^2$ represents a hydrogen atom; a $C_1$-$C_{10}$ alkyl radical, linear or branched, non-substituted or substituted by at least one group chosen from among —OH, —C(O)OH, —NH$_2$, —C(O)H,

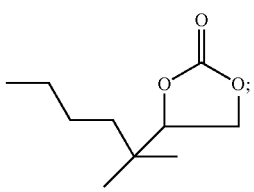

a $C_3$ to $C_8$ carbo- or heterocycle,
$R^3$ is:
 a hydroxyl group (OH),
 an alkoxy group of —OX type, with X chosen from among a $C_1$-$C_{20}$ alkyl, linear or branched, optionally substituted by at least one group selected from the group consisting of —OH, —C(O)OH, —NH$_2$, —C(O)H, and

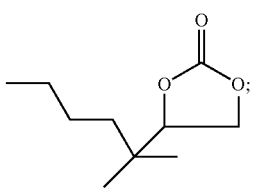

a —NY'Y" amine group where Y' and Y", the same or different represent a hydrogen atom, a $C_1$-$C_{20}$ alkyl, linear or branched, optionally substituted by at least one group selected from the group consisting of —OH, —C(O)OH, —NH$_2$, —C(O)H, and

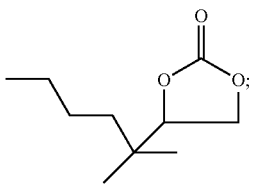

a thio group of SZ type, with Z is a $C_1$-$C_{20}$ alkyl, linear or branched, optionally substituted by at least one group selected from the group consisting of —OH, —C(O)OH, —NH$_2$, —C(O)H, and

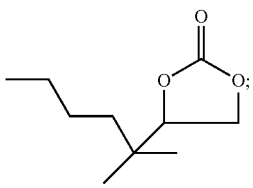

$R^4$ is:
an oxygen atom; or
a nitrogen atom;
$R^5$ is:
a $C_1$-$C_{20}$ alkyl group, linear or branched, optionally substituted by at least one group selected from the group consisting of —OH, —C(O)OH, —NH$_2$, —C(O)H, and

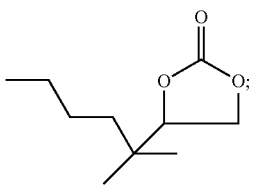

l is an integer between 1 and 10;
m is an integer between 1 and 3; and
p is an integer between 0 and 10.

2. The fatty substance according to claim 1 in which G, the same or different, represents
—NR$^1$H; —C(O)OH; or

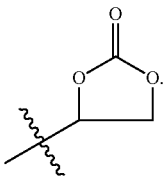 [SMILES: *C1COC(=O)O1]

3. A method for preparing a functionalized fatty substance comprising the reaction of a fat of natural origin chosen from among:
vegetable oils comprising at least two unsaturations and their derivatives;
fatty acids comprising at least one unsaturation and their derivatives;
the mixtures thereof
with a thiol derivative of formula (I)

$$G_nL^1\text{-}L^2\text{-SH} \qquad (I)$$

in which:
G, the same or different, represents —NR$^1$H; —C(O)OH;

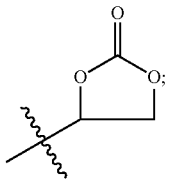

or —C(O)H;
n is 1 or 2;
$R^1$ is a hydrogen atom; a $C_1$-$C_{10}$ alkyl radical non-substituted or substituted by at least one group selected from the group consisting of —OH, —C(O)OH, —NH$_2$, —C(O)H, and

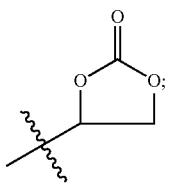 [SMILES: *C1COC(=O)O1]

$L^1$ is a —CH$_2$ group; a direct bond;
$L^2$ is:
a $C_1$-$C_{20}$ alkyl, linear or branched, optionally comprising one or more heteroatoms selected from the group consisting of an oxygen atom, a nitrogen atom, and a sulfur atom, non-substituted or substituted by at least one group selected from the group consisting of —OH, —C(O)OH, —C(O)H,

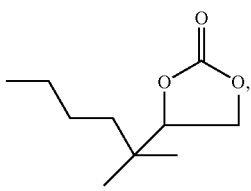

and —NHR$^2$ where $R^2$ is a hydrogen atom; or a $C_1$-$C_{10}$ alkyl radical, linear or branched, non-substituted or substituted by at least one group selected from the group consisting of —OH, —C(O)OH, —NH$_2$, —C(O)H, and

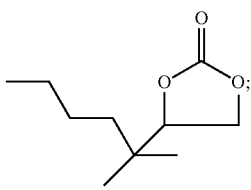

a $C_3$ to $C_8$ carbo- or heterocycle;
at a temperature of between 0° C. and the total degradation temperature of the natural fatty substance and in the presence of a thermal initiator or a redox initiator, or under the action of UV radiation, or
under the action of UV radiation in the presence of a photoinitiator.

4. The method according to claim 3 in which the vegetable oil and the derivatives thereof comprise between 2 and 20 unsaturations.

5. The method according to claim 3 in which the vegetable oil is selected from the group consisting of natural crude or purified vegetable oils, and vegetable oils derived from genetically modified plants or cultures.

6. The method according to claim 5 in which the vegetable oil is selected from the group consisting of canola oil, safflower oil, rapeseed oil, cottonseed oil, linseed oil, corn oil, hazelnut oil, coconut oil, olive oil, palm oil, grape-seed oil, castor oil, sesame oil, soybean oil, and sunflower oil, alone or in a mixture.

7. The method according to claim 3 in which the derivatives of vegetable oils are fatty esters obtained by esterification or transesterification of the vegetable oils in claim 4, fatty amides obtained by amidification or transamidification of the vegetable oils in claim 4, partly epoxidated oils.

8. The method according to claim 3 in which the fatty acids and their derivatives comprise between 1 and 6 unsaturations.

9. The method according to claim 3 in which the fatty acids and their derivatives are selected from the group consisting of arachidonic acid, docosahexaenoic acid, eicosapentaenoic acid, erucic acid, linoleic acid, linolenic acid, nervonic acid, oleic acid, palmitoleic acid, ricinoleic acid, vernolic acid; the esters of fatty acids; the fatty amides obtained by amidification of fatty acids and the fatty thioesters derived from thioesterification of fatty acids; the fatty acids obtained from the vegetable oils selected from the group consisting of canola oil, safflower oil, rapeseed oil, cotton oil, linseed oil, corn oil, hazelnut oil, coconut oil, olive oil, palm oil, grape-seed oil, castor oil, sesame oil, soybean oil, and sunflower oil, alone or in a mixture; alone or in a mixture.

10. The method according to claim 3 in which G, the same or different, represents —NR$^1$H; or —C(O)OH.

11. The method according to claim 3 in which G, the same or different, represents —C(O)OH, —NH$_2$, —C(O)H.

12. The method according to claim 3 in which the thiol derivative of formula (I) is selected from the group consisting of cysteamine (2-aminoethanethiol), thioglycolic acid (mercaptoacetic acid), β-mercaptoethanol, mercaptosuccinic acid (thiomalic acid), 3-mercaptopropionic acid, 1-thiolglycerol (3-mercapto-1,2-propanediol), cysteine, 3-mercapto-1-propanol, 4-mercapto-1-butanol, 4-mercaptophenol, 4-aminothiophenol, 6-mercaptohexanoic acid, 3-mercaptobenzoic acid, thiosalicylic acid, 2-mercapto-benzyl alcohol, 4-mercaptophenylacetic acid, 8-mercaptooctanoic acid, 9-mercapto-1-nonanol, 12-mercaptododecanoic acid, 3-mercaptobutanal, and 3-mercaptohexanal.

13. The method according to claim 3 in which the temperature is between ambient temperature and the total degradation temperature of the natural fatty substance.

14. The method according to claim 13 in which the temperature is between 40° C. and 250° C.

15. A functionalized fatty substance obtained by the method of claim 3.

16. A method of preparing a polymer, comprising the implementation of a functionalized fatty substance according to claim 1.

17. The method according to claim 16 for preparing a polymer selected from the group consisting of polyesters, polyamides, polycarbamates, polyisocyanates, and epoxy resins.

18. The method according to claim 16 comprising the following steps:
(a1) preparation of a functionalized fatty substance comprising the reaction of a fat of natural origin selected from the group consisting of:
vegetable oils comprising at least two unsaturations and their derivatives;
fatty acids comprising at least one unsaturation and their derivatives; and
mixtures thereof
with a thiol derivative of formula (I)

$$G_n L^1 \text{-} L^2 \text{-SH} \qquad (I)$$

in which:
G, the same or different, represents —NR$^1$H; —C(O)OH;

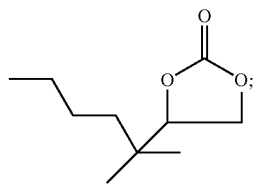

—C(O)H;
n is 1 or 2;
R$^1$ is a hydrogen atom; a C$_1$-C$_{10}$ alkyl radical non-substituted or substituted by at least one group selected from the group consisting of —OH, —C(O)OH, —NH$_2$, —C(O)H, and

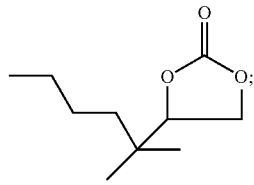

L$^1$ is a —CH$_2$ group; a direct bond;
L$^2$ is:
a C$_1$-C$_{20}$ alkyl, linear or branched, optionally comprising one or more heteroatoms selected from the group consisting of an oxygen atom, a nitrogen atom, and a sulfur atom, non-substituted or substituted by at least one group selected from the group consisting of —OH, —C(O)OH, —C(O)H,

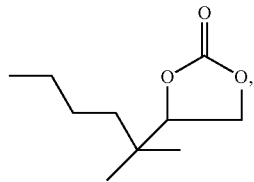

and —NHR$^2$ where R$^2$ is a hydrogen atom; a C$_1$-C$_{10}$ alkyl radical, linear or branched, non-substituted or substituted by at least one group selected from the group consisting of —OH, —C(O)OH, —NH$_2$, —C(O)H, and

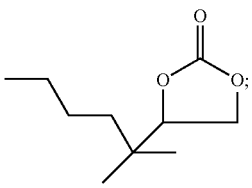

a C₃ to C₈ carbo- or heterocycle;
at a temperature of between 0° C. and the total degradation temperature of the natural fatty substance and in the presence of a thermal initiator or a redox initiator, or
under the action of UV radiation, or
under the action of UV radiation in the presence of a photoinitiator; and
(a2) polycondensation between the functionalized fatty substance obtained at step (a1) and at least one molecule, at least bifunctional, selected from the group consisting of isocyanates, alcohols, carboxylic acids, amines, carbamates, aldehydes, and epoxy.

19. The method according to claim 16 comprising the following steps:
(b1) preparation of a functionalized fatty substance comprising the reaction of a fat of natural origin selected from the group consisting of:
vegetable oils comprising at least two unsaturations and their derivatives;
fatty acids comprising at least one unsaturation and their derivatives; and
mixtures thereof
with a thiol derivative of formula (I)

$$G_n L^1\text{-}L^2\text{-SH} \qquad (I)$$

in which:
G, the same or different, represents —NR¹H; —C(O)OH;

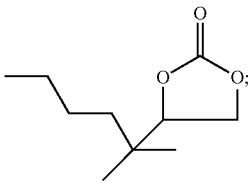

or —C(O)H;
n is 1 or 2;
R¹ is a hydrogen atom; a $C_1$-$C_{10}$ alkyl radical non-substituted or substituted by at least one group selected from the group consisting of —OH, —C(O)OH, —NH₂, —C(O)H, and

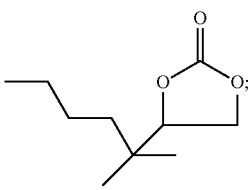

$L^1$ is a —CH₂ group; a direct bond;
$L^2$ is:
a $C_1$-$C_{20}$ alkyl, linear or branched, optionally comprising one or more heteroatoms selected from the group consisting of an oxygen atom, a nitrogen atom, and a sulfur atom, non-substituted or substituted by at least one group selected from the group consisting of —OH, —C(O)OH, —C(O)H,

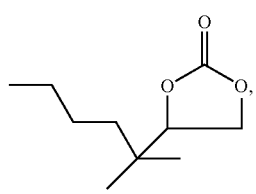

and —NHR² where R² is a hydrogen atom; a $C_1$-$C_{10}$ alkyl radical, linear or branched, non-substituted or substituted by at least one group selected from the group consisting of —OH, —C(O)OH, —NH₂, —C(O)H, and

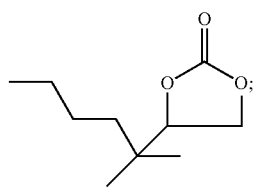

a C₃ to C₈ carbo- or heterocycle;
at a temperature of between 0° C. and the total degradation temperature of the natural fatty substance and in the presence of a thermal initiator or a redox initiator, or
under the action of UV radiation, or
under the action of UV radiation in the presence of a photoinitiator; and
(b2) preparation of a second functionalized fatty substance according to step (b1) different and in which the function G is different from that of the fatty substance prepared at step (b1), then
(b3) polycondensation between the two functionalized fatty substances.

20. The fatty substance according to claim 1 wherein the C₃ to C₈ carbo- or heterocycle is selected from the group consisting of a cycloaliphatic group, an aryl group, and a heteroaryl group.

21. The fatty substance according to claim 1 in which G, the same or different, represents —NR¹H or —C(O)OH.

22. The method for preparing a functionalized fatty substance according to claim 3 wherein the C₃ to C₈ carbo- or heterocycle is selected from the group consisting of a cycloaliphatic group, an aryl group, and a heteroaryl group.

23. The method according to claim 19 wherein the C₃ to C₈ carbo- or heterocycle is selected from the group consisting of a cycloaliphatic group, an aryl group, and a heteroaryl group.

* * * * *